United States Patent [19]
Karavidas

[11] Patent Number: 6,013,088
[45] Date of Patent: Jan. 11, 2000

[54] SURGICAL CLAMP WITH REMOVABLE TIPS

[76] Inventor: Theocharis Karavidas, 1 Point Cresent Malba, New York, N.Y. 11357

[21] Appl. No.: 09/193,820

[22] Filed: Nov. 17, 1998

[51] Int. Cl.⁷ .................................................... A61B 17/08
[52] U.S. Cl. ........................................... 606/157; 606/205
[58] Field of Search ................................... 606/157, 158, 606/138, 139, 142, 205, 143, 148

[56] References Cited

U.S. PATENT DOCUMENTS

| | | | |
|---|---|---|---|
| 3,326,216 | 6/1967 | Wood. | |
| 3,867,944 | 2/1975 | Samuels | 128/325 |
| 4,424,810 | 1/1984 | Jewusiak | 128/326 |
| 4,449,531 | 5/1984 | Cerwin | 128/325 |
| 4,527,562 | 7/1985 | Mericle | 128/325 |
| 5,036,733 | 8/1991 | Tiholiz et al. | 606/205 |
| 5,868,835 | 2/1999 | Lolagne | 606/205 |

*Primary Examiner*—Michael Buiz
*Assistant Examiner*—Vy Q. Bui
*Attorney, Agent, or Firm*—Goldstein & Canino

[57] ABSTRACT

A surgical clamp with removable tips including a forceps-type ligating clip applier including a pair of handle members coupled together at a hinged member. Each of the handle members have a gripping member extending outwardly therefrom. Each gripping member has serrated teeth formed on inner surfaces thereof. Upper ends of the handle members each have locking tabs extending inwardly thereof for mating when the gripping members are in an abutting relationship. A pair of disposable clip members removably couple with the gripping members of the clip applier.

4 Claims, 2 Drawing Sheets

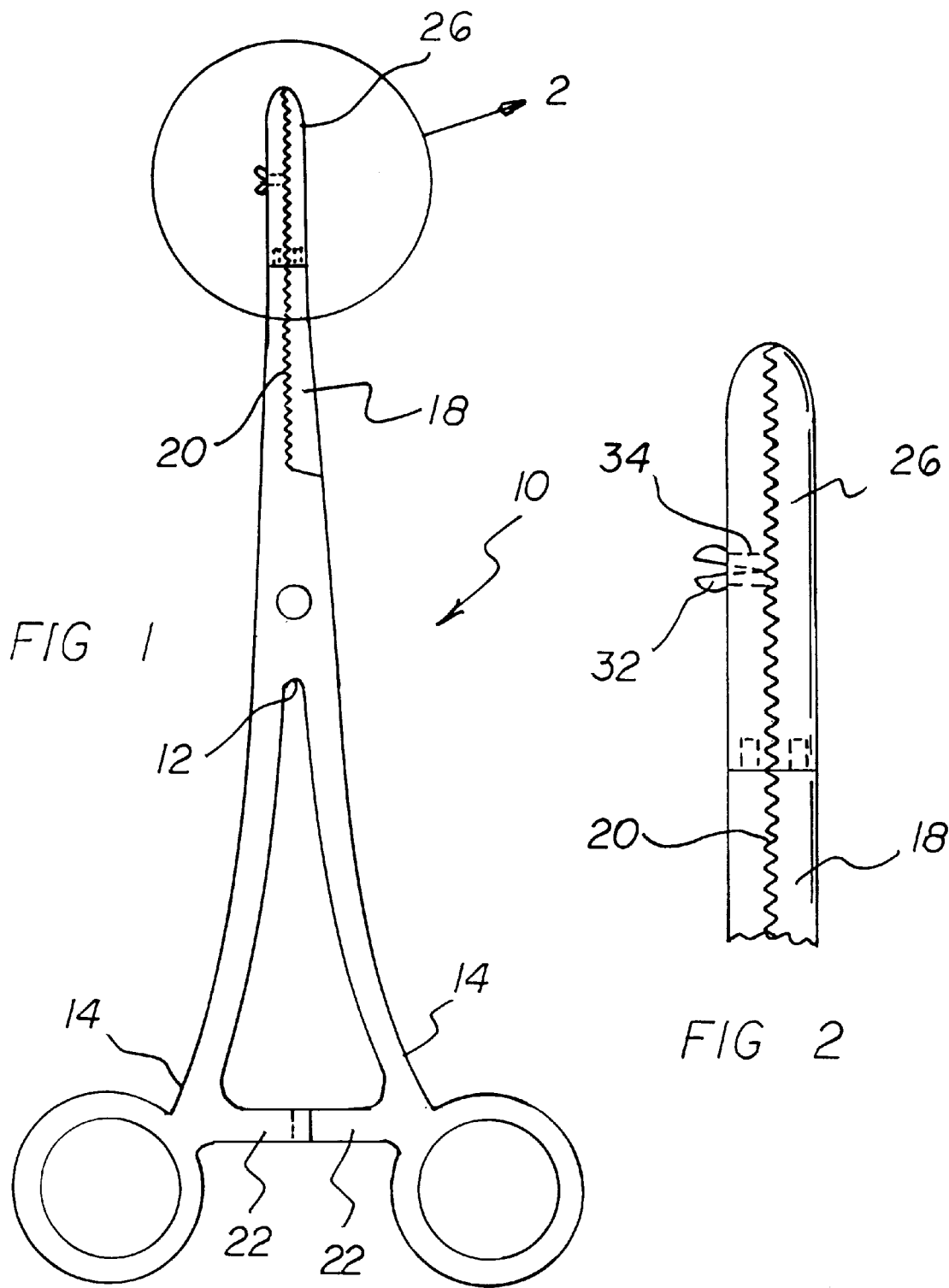

SURGICAL CLAMP WITH REMOVABLE TIPS

BACKGROUND OF THE INVENTION

1. Field of the Invention

The present invention relates to a surgical clamp with removable tips and more particularly pertains to shortening an operative time by avoiding suture ligatures with a surgical clamp with removable tips.

2. Description of the Prior Art

The use of surgical clamps is known in the prior art. More specifically, surgical clamps heretofore devised and utilized for the purpose of clipping blood vessels and the like are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,326,216 to Wood; U.S. Pat. No. 4,449,531 to Cerwin; U.S. Pat. No. 3,867,944 to Samuels; and U.S. Patent Number to Mericle.

While these devices fulfill their respective, particular objective and requirements, the aforementioned patents do not describe a surgical clamp with removable tips for shortening an operative time by avoiding suture ligatures.

In this respect, the surgical clamp with removable tips according to the present invention substantially departs from the conventional concepts and designs of the prior art, and in doing so provides an apparatus primarily developed for the purpose of shortening an operative time by avoiding suture ligatures.

Therefore, it can be appreciated that there exists a continuing need for new and improved surgical clamp with removable tips which can be used for shortening an operative time by avoiding suture ligatures. In this regard, the present invention substantially fulfills this need.

SUMMARY OF THE INVENTION

In the view of the foregoing disadvantages inherent in the known types of surgical clamps now present in the prior art, the present invention provides an improved surgical clamp with removable tips. As such, the general purpose of the present invention, which will be described subsequently in greater detail, is to provide a new and improved surgical clamp with removable tips and method which has all the advantages of the prior art and none of the disadvantages.

To attain this, the present invention essentially comprises a forceps-type ligating clip applier including a pair of handle members coupled together at a hinged member. Each of the handle members have a gripping member extending outwardly therefrom. Each gripping member has serrated teeth formed on inner surfaces thereof. Upper ends of the handle members each have locking tabs extending inwardly thereof for mating when the gripping members are in an abutting relationship. Outer ends of the gripping members each have an extension extending linearly therefrom. A pair of disposable clip members removably couple with the gripping members of the clip applier. The clip members each have a recess formed in a lower end thereof for receiving the extensions of the gripping members therein. Each of the clip members have serrated teeth formed on inner surfaces thereof. An upper clip member has a bulbous split protrusion extending outwardly from the inner surface thereof. A lower clip member has an aperture therethrough for receiving the bulbous split protrusion therein in a locked orientation.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved surgical clamp with removable tips which has all the advantages of the prior art surgical clamps and none of the disadvantages.

It is another object of the present invention to provide a new and improved surgical clamp with removable tips which may be easily and efficiently manufactured and marketed.

It is a further object of the present invention to provide a new and improved surgical clamp with removable tips which is of durable and reliable construction.

An even further object of the present invention is to provide a new and improved surgical clamp with removable tips which is susceptible of a low cost of manufacture with regard to both materials and labor, and which accordingly is then susceptible of low prices of sale to the consuming public, thereby making such a surgical clamp with removable tips economically available to the buying public.

Even still another object of the present invention is to provide a new and improved surgical clamp with removable tips for shortening an operative time by avoiding suture ligatures.

Lastly, it is an object of the present invention to provide a new and improved surgical clamp with removable tips including a forceps-type ligating clip applier including a pair of handle members coupled together at a hinged member. Each of the handle members have a gripping member extending outwardly therefrom. Each gripping member has serrated teeth formed on inner surfaces thereof. Upper ends of the handle members each have locking tabs extending inwardly thereof for mating when the gripping members are in an abutting relationship. A pair of disposable clip members removably couple with the gripping members of the clip applier.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the surgical clamp with removable tips constructed in accordance with the principles of the present invention.

FIG. 2 is an enlarged front view of the present invention as taken from circle 2 of FIG. 1.

The same reference numerals refer to the same parts through the various figures.

DESCRIPTION OF THE PREFERRED EMBODIMENT

Figures 3, 4:
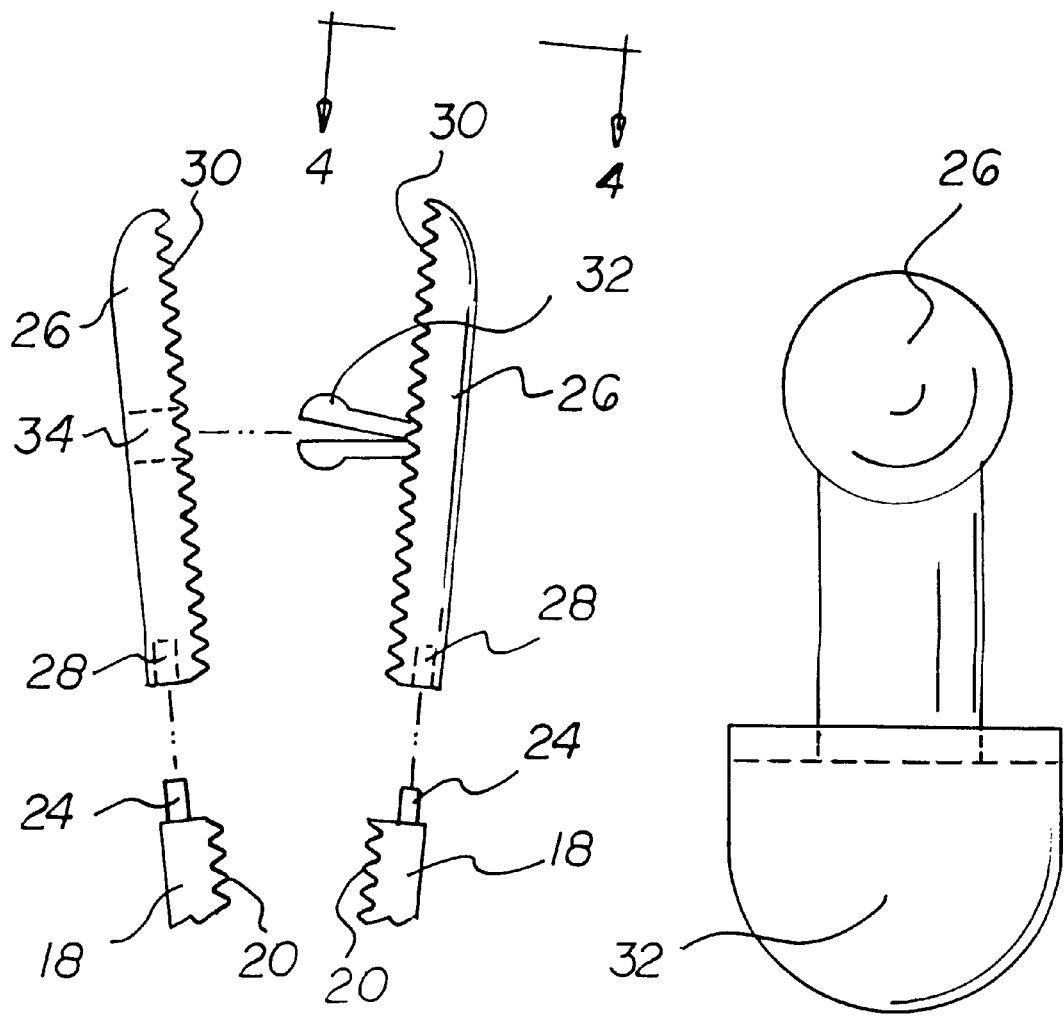
FIG. 3 is a partial view of the present invention illustrating the removable tips.
FIG. 4 is an end view of the present invention as taken along line 4—4 of FIG. 3.

With reference now to the drawings, and in particular, to FIGS. 1 through 4 thereof, the preferred embodiment of the new and improved surgical clamp with removable tips embodying the principles and concepts of the present invention and generally designated by the reference number 10 will be described.

Specifically, it will be noted in the various Figures that the device relates to a surgical clamp with removable tips for shortening an operative time by avoiding suture ligatures. In its broadest context, the device consists of a ligating clip applier and a pair of disposable clips. Such components are individually configured and correlated with respect to each other so as to attain the desired objective.

The forceps-type ligating clip applier 12 including a pair of handle members 14 coupled together at a hinged member 16. Each of the handle members 14 have a gripping member 18 extending outwardly therefrom. Each gripping member 18 has serrated teeth 20 formed on inner surfaces thereof. Upper ends of the handle members 14 each have locking tabs 22 extending inwardly thereof for mating when the gripping members 18 are in an abutting relationship. Outer ends of the gripping members 18 each have an extension 24 extending linearly therefrom.

The pair of disposable clip members 26 removably couple with the gripping members 18 of the clip applier 12. The clip members 26 each have a recess 28 formed in a lower end thereof for receiving the extensions 24 of the gripping members 18 therein. Each of the clip members 26 have serrated teeth 30 formed on inner surfaces thereof. An upper clip member has a bulbous split protrusion 32 extending outwardly from the inner surface thereof. A lower clip member has an aperture 34 therethrough for receiving the bulbous split protrusion 32 therein in a locked orientation. The clip members 26 are preferably fabricated of a plastic material.

In use, once the clip members 26 are locked into a ligature, the clip applier 12 can be removed by detaching the clip members 26 therefrom. After use, the clip members 26 can be disposed of properly.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A surgical clamp with removable tips for shortening an operative time by avoiding suture ligatures comprising, in combination:

a forceps-type ligating clip applier including a pair of handle members coupled together at a hinged member, each of the handle members having a gripping member extending outwardly therefrom, each gripping member having serrated teeth formed on inner surfaces thereof, upper ends of the handle members each having locking tabs extending inwardly thereof for mating when the gripping members are in an abutting relationship, outer ends of the gripping members each having an extension extending linearly therefrom;

a pair of disposable clip members removably coupling with the gripping members of the clip applier, the clip members each having a recess formed in a lower end thereof for receiving the extensions of the gripping members therein, each of the clip members having serrated teeth formed on inner surfaces thereof, an upper clip member having a bulbous split protrusion extending outwardly from the inner surface thereof, a lower clip member having an aperture therethrough for receiving the bulbous split protrusion therein in a locked orientation.

2. A surgical clamp with removable tips for shortening an operative time by avoiding suture ligatures comprising, in combination:

a forceps-type ligating clip applier including a pair of handle members coupled together at a hinged member, each of the handle members having a gripping member extending outwardly therefrom, each gripping member having serrated teeth formed on inner surfaces thereof, upper ends of the handle members each having locking tabs extending inwardly thereof for mating when the gripping members are in an abutting relationship;

a pair of disposable clip members removably coupling with the gripping members of the clip applier, each of the clip member having serrated teeth formed on inner surfaces thereof, an upper clip member having a bulbous split protrusion extending outwardly from the inner surface thereof, a lower clip member having aperture therethrough for receiving the bulbous split protrusion therein in a locked orientation.

3. The surgical clamp with removable tips as set forth in claim 2 wherein outer ends of the gripping members each having an extension extending linearly therefrom for engaging the clip members.

4. The surgical clamp with removable tips as set forth in claim 2 wherein the clip members each have a recess formed in a lower end thereof for receiving the upper ends of the gripping members therein.

* * * * *